United States Patent
Frauenschuh

(10) Patent No.: US 9,663,552 B2
(45) Date of Patent: May 30, 2017

(54) PURIFICATION METHOD FOR PROTEINS, IN PARTICULAR ANTIBODIES, UTILIZING A WASH SOLUTION COMPRISING ARGININE AT HIGH PH FOR THE AFFINITY CHROMATOGRAPHY STEP

(75) Inventor: Achim Frauenschuh, Werentzhouse (FR)

(73) Assignee: Novartis AG, Basel (CH)

( * ) Notice: Subject to any disclaimer, the term of this patent is extended or adjusted under 35 U.S.C. 154(b) by 464 days.

(21) Appl. No.: 14/122,707

(22) PCT Filed: May 31, 2012

(86) PCT No.: PCT/EP2012/060313
§ 371 (c)(1),
(2), (4) Date: Nov. 27, 2013

(87) PCT Pub. No.: WO2012/164046
PCT Pub. Date: Dec. 6, 2012

(65) Prior Publication Data
US 2014/0094593 A1    Apr. 3, 2014

Related U.S. Application Data

(60) Provisional application No. 61/492,092, filed on Jun. 1, 2011.

(51) Int. Cl.
C07K 1/00    (2006.01)
C07K 1/22    (2006.01)
(52) U.S. Cl.
CPC ....................................... *C07K 1/22* (2013.01)
(58) Field of Classification Search
None
See application file for complete search history.

(56) References Cited

U.S. PATENT DOCUMENTS

2005/0287210 A1* 12/2005 Ron .................... A61K 9/1635
                                                                   424/468
2012/0283416 A1* 11/2012 Frauenschuh .......... C07K 16/00
                                                                   530/387.3

FOREIGN PATENT DOCUMENTS

| EP | 0333474 A2 | 3/1989 |
| WO | 2008031020 A2 | 3/2008 |
| WO | 2011073389 A1 | 6/2011 |

OTHER PUBLICATIONS

"Affi-Prep Protein A amtrix: Instruction Manual" LIT230 rev B, , Bio Rad Laboratories, 2000, pp. 1-7.*
Yumioka et al. "Screening of effective column rinse solvent for Protein-A chromatography" Protein Expression and Purification 70 (2010) 218-223.*
IP.com Prior Art Database Technical Disclosure IPCOM000127319D, Aug. 22, 2005, entited "improving purity on protein A affinity chromatography media through use of an arginine intermediate wash step" by Barron et al., Millipore Corporation.*
Ritzen et al; Endotoxin reduction in monoclonal antibody, Journal of Chromatography, Elsevier, ISSN 1570-0232; vol. 856, No. 1-2, pp. 343-347.

* cited by examiner

*Primary Examiner* — Daniel E Kolker
*Assistant Examiner* — James Rogers
(74) *Attorney, Agent, or Firm* — Jason Derry

(57) ABSTRACT

The invention provides a washing method for affinity chromatography in which a wash solution comprising arginine, or an arginine derivative, at pH greater than 8.0, is effective in removing impurities without the presence of a nonbuffering salt, while simultaneously increasing product concentration in the eluate and maintaining a high percent yield of recovered product.

13 Claims, No Drawings

PURIFICATION METHOD FOR PROTEINS, IN PARTICULAR ANTIBODIES, UTILIZING A WASH SOLUTION COMPRISING ARGININE AT HIGH PH FOR THE AFFINITY CHROMATOGRAPHY STEP

BACKGROUND OF THE INVENTION

The efficient removal of impurities during affinity chromatography, including host cell proteins (HCPs) and product-related impurities, such as high (HMWs) and low (LMWs) molecular weight species, is a crucial factor during downstream processing of proteins. The purity of the protein after the first purification step (the "capture step"), notably influences the type and number of subsequent steps required to generate a purified product. The capture step is also critical because it concentrates the product, which allows for the use of proportionally smaller, less costly columns in subsequent purification steps. Therefore, it is important to optimize the removal of impurities during the first chromatography step. In the case of antibody purification, this first step is typically based on affinity to protein A or derivatives.

Low pH conditions (e.g., between pH 3-4) are required to elute bound target protein from the affinity column, but have the disadvantage of potentially inducing aggregation. Historically, less stringent conditions, such as a pH between 5-5.5 have been used to wash non-specifically bound impurities from the column, while simultaneously preserving the target-protein A interaction. The recovery, however, is often decreased due to partial elution of the target protein under these conditions, particularly when working at high loading densities.

The amino acid arginine has been shown to solubilize certain precipitated proteins (M, Tsumoto K, Nitta S, Adschiri T, Ejima D, Arakawa T, and Kumagai I. Biochem. Biophys. Res. Commun. 328, 189-197 (2005); Umetsu M, Tsumoto K, Hara M, Ashish K, Goda S, Adschiri T, Kumagai I. J Biol Chem. 2003 Mar. 14; 278(11):8979-87), reduce the formation of aggregates (Arakawa T, Tsumoto K. Biochem Biophys Res Commun. 2003 Apr. 25; 304(1):148-52) and Arakawa T, *Biophys. Chem.* 127 (2007), pp. 1-8 (Review)) and reduce nonspecific adsorption of proteins to surfaces (Ejima D, J Chromato A, 05 and Schneider C P, *J. Phys. Chem. B* 113 (2009), pp. 2050-2058). Moreover, in contrast to guanidium hydrochloride, arginine has not been shown not to unfold proteins (Arakawa T, *Biochem. Biophys. Res. Commun.* 304 (2003), pp. 148-152 and Nakakido M, *Biophys. Chem.* 137 (2008), pp. 105-109).

As such, arginine has been used to elute proteins from affinity chromatography columns and other types of purification columns. For example, Arakawa et al. describe methods of eluting antibodies from a Protein A column using an elution buffer containing 0.5-2.0 M arginine at pH 4.1-5.0 (Arakawa et al. (2004) *Protein Expression and Purification* 36:244-248; Tsumoto, K. et al. (2004) *Biotechnol. Prog.* 20:1301-1308; U.S. Patent Publication No. 20050176109). Additionally, U.S. Pat. No. 7,501,495 by Ejima et al. describes methods of eluting proteins from a gel filtration column by a developing solution containing arginine hydrochloride. Ghose et al. describe methods of eluting proteins of interest from underivatized silica using an arginine gradient as the eluant (Ghose, S. et al. (2004) *Biotech. Bioeng.* 87:413-423). U.S. Patent Publication No. 20030050450 by Coffman et al. describes methods of dissociating Fc containing molecules from complexes of the Fc containing molecule and Protein A, wherein the Fc/Protein A complexes are applied to a hydrophobic interaction column (HIC) and the column is washed with a buffer containing arginine.

Barron et al. describe an intermediate wash solution for Protein A chromatography containing 0.5 to 2.0 M arginine in a phosphate/acetate buffer at pH 5.0-7.5 (optimally 1M arginine, 0.1M phosphate/acetate buffer at pH 5.0). This arginine wash step is reported to remove HCP contaminants. The authors also tested an intermediate wash solution that contained sodium chloride at 0.5-2.0 M at pH 5.0-7.5, and reported that the NaCl wash showed no significant decrease in HCP (Barron et al., "Improving Purity on Protein A Affinity Media Through Use of an Arginine Intermediate Wash Step", http://www.priorartdatabase.com/IPCOM/000127319). Moreover, Barron et al. reported that lowering the pH of the wash buffer had a beneficial effect under the conditions used in the experiment.

There is a longstanding need for improved techniques to enhance the purification process and increase product recovery. The present disclosure addresses this need and provides additional benefits.

SUMMARY OF THE INVENTION

This invention provides an efficient and robust wash solution for affinity chromatography, as well as washing methods using this solution. This wash solution is applied in a washing step prior to the elution step, and its use effectively removes low molecular weight species (LMWs), high molecular weight species (HMWs), and host cell proteins (HCPs) from the starting material applied to the matrix, while resulting in high yields of the protein of interest eluted from the affinity matrix. This wash solution is characterized by the presence of arginine at high pH, i.e., above 8.0, without the presence of a nonbuffering salt. This combination of arginine (or an arginine derivative) at high pH removes significantly more impurities than wash solutions containing arginine at lower pH and results in a sharper elution peak correlating with a high concentration of the recovered protein of interest.

Accordingly, in one embodiment, the invention provides a method of producing a purified protein of interest (e.g., an antibody, antibody fragment, or protein) using an affinity chromatography (AC) matrix to which the protein of interest is bound, the method comprising washing the AC matrix with a wash solution comprising arginine, or an arginine derivative, at a pH of greater than 8.0, without the presence of a nonbuffering salt. In a preferred embodiment, the pH of the wash solution is at least 8.1, more preferably at least 8.5, and even more preferably at least 8.9 or 9.0. In one embodiment, the pH of the wash solution is about 8.5-9.5. In another embodiment, the pH of the wash solution is about 8.9-9.0.

In another embodiment, the method further comprises (a) loading a mixture comprising the protein of interest onto the AC matrix, (b) washing the AC matrix with a wash solution comprising arginine, or an arginine derivative, at a pH greater than 8.0; and (c) eluting the protein of interest from the AC matrix, wherein the wash is performed without the presence of a nonbuffering salt.

In a particular embodiment, the AC matrix is a Protein A column. In various other embodiments, the AC matrix is selected from the group consisting of a Protein G column, a Protein A/G column, a Protein L column, an immobilized metal ion affinity chromatography (IMAC) column, a calmodulin resin column, a MEP HyperCel™ column, a column that binds maltose binding protein (MBP), a column that binds glutathione-S-transferase (GST), a column that binds Strep-Tag II, and a dye-affinity column. In other embodiments, the AC matrix comprises a resin selected from the group consisting of CaptureSelect IgG-CH1, CaptureSelect IgG-Fc (Hu), CaptureSelect LC-kappa (Hu), CaptureSelect LC-lambda (Hu), CaptureSelect IgG4 (Hu), CaptureSelect IgG1 (Hu), CaptureSelect IgG3 (Hu), CaptureSelect IgM and CaptureSelect IgA. In other embodiments, the AC matrix comprises a resin selected from the group consisting of IgSelect, KappaSelect, LamdaFabSelect, and Capto L.

Suitable proteins of interest include, but are not limited to, antibodies (and other proteins comprising Fc regions, such as Fc fusion proteins) and antibody fragments, although other proteins that bind to the affinity matrices described herein are also suitable for purification according to the methods of the invention.

In another aspect, the invention provides a method of producing a purified antibody, antibody fragment, or protein comprising an Fc region (e.g., an Fc fusion protein), using a Protein A column, the method comprising (a) loading a mixture comprising the antibody, antibody fragment, or protein, onto the Protein A column; (b) washing the Protein A column with a wash solution comprising (i) arginine, or an arginine derivative, at a pH of greater than 8.0 (e.g., about 8.5-9.5 or about 8.9-9.0); and (c) eluting the antibody, antibody fragment, or protein, from the Protein A column, wherein the wash is performed without the presence of a nonbuffering salt.

In yet another aspect, the method optionally includes equilibrating the Protein A column prior to loading and/or eluting the protein of interest (e.g., an antibody, antibody fragment, or protein comprising an Fc region (e.g., an Fc fusion protein)) from the Protein A column. For example, the invention provides a method of producing a purified antibody, antibody fragment, or protein comprising an Fc region (e.g., an Fc fusion protein) using a Protein A column, the method comprising (a) equilibrating the Protein A column (e.g., using an equilibration buffer, to adjust pH and remove any residual storage buffer); (b) loading a mixture comprising the antibody, antibody fragment, or protein onto the Protein A column; (c) washing the Protein A column with a wash solution comprising (i) arginine, or an arginine derivative, at a pH of greater than 8.0 (e.g., about 8.5-9.5 or about 8.9-9.0); and (d) eluting the antibody, antibody fragment, or protein from the Protein A column, wherein the wash is performed without the presence of a nonbuffering salt. The method may further comprise the step of equilibrating the Protein A column prior to eluting the antibody, antibody fragment, or protein.

In a particular embodiment, the wash solution comprises arginine or arginine-HCl, preferably at a concentration in a range of about 0.1-0.5 M. In another particular embodiment, arginine or arginine-HCl is present at a concentration of 0.25 M or about 0.25 M. In still other particular embodiments, the wash solution comprises an arginine derivative, such as a derivative selected from the group consisting of acetyl arginine, N-alpha-butyroyl-arginine, agmatine, arginic acid and N-alpha-pyvaloyl arginine.

The method of the invention is effective in removing a variety of impurities, including high and low molecular weight (HMW and LMW, respectively) species and host cell proteins (HCPs). In a particular embodiment, the wash solution further comprises one or more buffering salts (e.g., sodium acetate, sodium phosphate or Tris).

DETAILED DESCRIPTION OF THE INVENTION

The invention provides an improved washing solution for affinity chromatography, such as Protein A chromatography, which is applied to the column prior to elution of the protein of interest to remove impurities. The improved washing solution comprises arginine, or an arginine derivative, at a pH of greater than 8.0 (e.g., a pH of greater than 8.1, preferably a pH of greater than 8.5, for example between about 8.5-9.5 or about 8.9-9.0), without the presence of a nonbuffering salt. Typically, the washing solution is an aqueous solution.

This unique combination of arginine, or an arginine derivative, at high pH removes significantly more impurities than commonly used procedures, without affecting recovery. In addition, this washing condition results in a sharper elution peak correlating with a higher concentration of the protein of interest in the eluate, which is advantageous to increase the performance of additional downstream purification processes.

Efficient removal of impurities, including host cell proteins (HCPs) and product-related impurities such as high molecular weight (HMW) species and low molecular weight (LMW) species, is a crucial factor during downstream processing of a protein of interest. Affinity chromatography is often used as the first stage of a multi-stage purification process for a protein of interest (e.g., an antibody) and the purity of the protein of interest after affinity chromatography notably influences the kind and number of subsequent purification steps. Another important role for affinity chromatography is to concentrate the product, which allows for the use of proportionally smaller, less costly columns and reservoirs (bags or steel tanks) in subsequent purification steps. Therefore, it is particularly important to optimize the removal of impurities during the affinity chromatography step whilst maintaining a high intermediate concentration and without compromising the yield.

Depending on the matrix, low pH conditions, typically between pH 3-4, are a requisite to elute the bound protein of interest from the affinity matrix and have the drawback of potentially inducing aggregation. Historically, less stringent conditions, such as pH 5-5.5, have been used to wash nonspecifically bound impurities from the column whilst preserving the interaction between the protein of interest and the affinity matrix. Recovery of the protein of interest, however, is often decreased due to partial elution of the protein of interest at these conditions, especially when working at high loading densities. Accordingly, in a preferred embodiment, the wash solution provided by the present invention is advantageously performed at a pH of greater than 8.0 (e.g., preferably a pH of greater than 8.1, more preferably a pH of greater than 8.5, for example between about 8.5-9.5 or about 8.9-9.0), which preserves binding of the protein of interest to the affinity matrix while allowing for removal of impurities.

Typically, arginine washes include nonbuffering salts. However, one advantage of the present invention is that the wash step employed in the invention does not require the presence of a nonbuffering salt. As used herein, the term "nonbuffering salt" refers to a salt that is of a type, and at a concentration, such that it does not substantially contribute to retaining the pH of a wash solution under the applied conditions (such as high pH) upon addition of acid or base. Nonbuffering salts include ionic salts, halogen salts, including those that comprise Cl or Br, and, in particular, halogen salts comprising alkali metals or alkaline earth metals, including sodium (Na), potassium (K), calcium (Ca) or magnesium (Mg), sodium (Na) or potassium (K) (i.e., NaCl, KCl, CaCl$_2$ and MgCl$_2$). In a particular embodiment, the wash is performed without the presence of NaCl.

The term "nonbuffering salt" does not include buffering salts, such as sodium acetate, sodium phosphate and Tris, that do substantially contribute to retaining the pH of a wash solution(s) under the applied conditions. Accordingly, such buffering salts may be included in the wash solutions of the invention.

The large biophysical diversity of impurities present in common harvests or cellular extracts results in very diverse modes of interactions with the solid phase of the chromatography medium and/or the bound protein of interest. More or less strong tethering of impurities may be the result of non-covalent intermolecular interactions between the two molecules, such as hydrogen bonding, electrostatic interactions, hydrophobic and Van der Waals forces or a combination of these types of interactions. Therefore, a combination of several different mechanisms (i.e., arginine, or an arginine derivative, in combination with a pH greater than 8.0) has been discovered to be more effective at removing impurities than traditional techniques.

In the context of using arginine in a wash solution, it has been reported that arginine has the ability to solubilize certain precipitated proteins (Umetsu, M. et al. (2005) *Biochem. Biophys. Res. Commun.* 328:189-197; Tsumoto, K. et al. (2003) *Biochem. Biophys. Res. Commun.* 312:1383-1386), reduce the formation of aggregates (Arakawa, T. et al. (2003) *Biochem. Biophys. Res. Commun.* 304:148-152), and reduce nonspecific adsorption of proteins to surfaces (Ejima, D. et al. (2005) *J. Chromatogr. A.* 1094:49-55). While not intending to be limited by mechanism, the reduction of protein aggregation may originate from the masking of hydrophobic patches on the proteins, which interact with arginine. This interaction may take place between the guanidium group on arginine and tryptophan groups on proteins, or through the formation of a hydrophobic patch by clustering of arginine, or may be a combination of such effects.

As used herein, the phrase "high pH" refers to a pH of greater than 8.0, which results in a significant reduction of impurities compared to a wash containing arginine or an arginine derivative at low or neutral pH (e.g., pH of about 5.0-7.0), as employed in previous wash methods. For example, in one embodiment, the "high pH" wash results in at least about a 2-3-fold reduction of HCPs, and/or at least about a 3-4-fold reduction of LMW levels, and/or an overall reduction in aggregation of at least about 30-50% or more, compared to an arginine-containing wash solution at low or neutral pH of 7.0.

In particular embodiments, the "high" pH of the wash solution is at least about 8.1, preferably at least about 8.5, and more preferably about 8.5-9.5 or about 8.9-9.0. Exemplary "high" pH conditions of the wash include, for example, pH values of 8.1 or about 8.1, 8.2 or about 8.2, 8.3 or about 8.3, 8.4 or about 8.4, 8.5 or about 8.5, 8.6 or about 8.6, 8.7 or about 8.7, 8.8 or about 8.8, 8.9 or about 8.9, 9.0 or about 9.0, 9.1 or about 9.1, 9.2 or about 9.2, 9.3 or about 9.3, 9.4 or about 9.4, 9.5 or about 9.5, 10.0 or about 10.0, 10.1 or about 10.1, 10.2 or about 10.2, 10.3 or about 10.3, 10.4 or about 10.4 and 10.5 or about 10.5. The wash solution also may contain one or more buffers (i.e., buffering salts) for adjusting and/or maintaining the pH. Non-limiting examples of typical buffers that can be included in the wash solution(s) include Tris (tris(hydroxymethyl)methylamine), bis-Tris, bis-Tris propane, histidine, triethanolamine, diethanolamine, formate, acetate, MES (2-(N-morpholino)ethanesulfonic acid), phosphate, HEPES (4-2-hydroxyethyl-1-piperazineethanesulfonic acid), citrate, MOPS (3-(N-morpholino)propanesulfonic acid), TAPS (3-{[tris (hydroxymethyl)methyl]amino}propanesulfonic acid), Bicine (N,N-bis(2-hydroxyethyl)glycine), Tricine (N-tris (hydroxymethyl)methylglycine), TES (2-{[tris(hydroxymethyl)methyl]amino}ethanesulfonic acid), PIPES (piperazine-N,N'-bis(2-ethanesulfonic acid), cacodylate (dimethylarsinic acid) and SSC (saline sodium citrate).

The purification method of the invention is effective in removing a variety of impurities, including high and low molecular weight (HMW and LMW, respectively) species and host cell proteins (HCPs). As described in detail in the Examples, the method is effective in reducing HMW species, LMW species, and HCPs in the wash eluate, while achieving a high percent yield of the protein of interest and a high concentration of the protein of interest. For example, in various embodiments, the method described herein results in a percent yield of the protein of interest that is greater than 97%, more preferably greater than 98%, most preferably greater than 99%.

In other embodiments, the method of the invention results in a percent reduction in HMW or LMW contaminants in the eluate that is at least about a 2-fold reduction, more preferably at least about a 3-fold reduction, more preferably at least about a 4-fold reduction, more preferably at least about a 5-fold reduction, and even more preferably at least about a 6-fold reduction. In still other embodiments, the method results in a logarithmic reduction value (LRV) of HCPs in the eluate of at least about 1.1, or at least about 1.2, or at least about 1.3, or at least about 1.4, or at least about 1.5, or at least about 1.6, or at least about 1.7, or at least about 1.8, or at least about 1.9, or at least about 2.0, or at least about 2.1, or at least about 2.2, or at least about 2.3, or at least about 2.4, or at least about 2.5, or at least about 2.6, or at least about 2.7, or at least about 2.8, or at least about 2.9, or at least about 3.0.

While not intending to be limited by mechanism, a high pH may partially denature HCPs and HMWs, whereas stable proteins, including monomeric antibodies, are not influenced at these conditions. Denaturing of contaminant proteins may be manifested as a slight change in structure, which may be sufficient to weaken nonspecific binding. Therefore, the high pH of the wash solution may be beneficial for increasing the removal of impurities by destabilizing their interaction with the bound protein of interest or the solid support of the affinity matrix.

Accordingly, in one aspect, the invention provide a method of producing a purified protein (e.g., an antibody, antibody fragment, or protein comprising an Fc region (e.g., an Fc fusion protein)) using an affinity chromatography (AC) matrix to which the protein of interest is bound, the method comprising washing the AC matrix with a wash solution comprising arginine, or an arginine derivative at a high pH of greater than 8.0 (e.g., preferably a pH of greater than 8.1, more preferably a pH of greater than 8.5, for example between about 8.5-9.5 or about 8.9-9.0), without the presence of a nonbuffering salt, prior to elution of the protein of interest from the AC matrix. The AC matrix optionally can be equilibrated prior to loading the protein of interest and/or prior to eluting the protein of interest.

As used herein, the term "affinity chromatography matrix" or "AC matrix", is intended to refer to a solid phase medium, typically a gel or resin, that allows for separation of biochemical mixtures based on a highly specific binding interaction between a protein of interest and the AC matrix, such as between a receptor and ligand, enzyme and substrate or antigen and antibody. Thus, the solid phase medium comprises a target to which the protein of interest is capable of reversibly affixing, depending upon the buffer conditions. Non-limiting examples of immobilized or solid phase media that can comprise the AC matrix include a gel matrix, such as agarose beads (such as commercially available Sepharose matrices), and a glass matrix, such as porous glass beads (such as commercially available ProSep matrices).

Binding of the protein of interest to the AC matrix typically is achieved by column chromatography. That is, the AC matrix is formed into a column, a biochemical mixture containing a protein of interest is flowed through the column, followed by washing of the column by flowing through the column a wash solution, followed by elution of the protein of interest from the column by flowing through the column an elution buffer.

Alternatively, binding of the protein of interest to the AC matrix can be achieved by batch treatment, in which the biochemical mixtures containing the protein of interest is incubated with the AC matrix in a vessel to allow for binding of the protein of interest to the AC matrix, the solid phase medium is removed from the vessel (e.g., by centrifugation or filtration using a vacuum pump), the solid phase medium is washed to remove impurities and again recovered (e.g., by centrifugation or filtration using a vacuum pump) and the protein of interest is eluted from the solid phase medium.

In yet another embodiment, a combination of batch treatment and column chromatography can be used. For example, the initial binding of the protein of interest to the AC matrix can be achieved by batch treatment and then the solid phase medium can be packed into a column, following by washing of the column and elution of the protein of interest from the column.

The nature of a particular solid phase matrix, in particular the binding properties of the target attached to the solid phase, determines the type(s) of protein(s) that can be purified using that solid phase matrix. For example, in a preferred embodiment of the invention, the AC matrix is a Protein A column, which comprises as the target attached to the solid phase a bacterial cell wall protein, Protein A, that specifically binds the CH2 and CH3 domains within the Fc region of certain immunoglobulins. The binding properties of Protein A are well established in the art.

Accordingly, in a preferred embodiment of the invention, the protein of interest (to be purified) is an antibody, antibody fragment, or protein comprising an Fc region (e.g., an Fc fusion protein). Furthermore, additional proteins that can be purified using Protein A chromatography include Fc containing proteins (e.g., Fc fusion proteins). Insofar as any protein is capable of specifically binding to a Protein A matrix, it can be purified according to the methods of the invention. Various Protein A resins are well known in the art and suitable for use in the invention. Non-limiting examples of commercially available Protein A resins include MabSelect, MabSelect Xtra, MabSelect Sure, rProtein A Sepharose FF, rmpProtein A Sepharose FF, Protein A Sepharose CL-4B and nProtein A Sepharose 4 FF (all commercially available from GE Healthcare); ProSep A, ProSep-vA High Capacity, ProSep-vA Ultra and ProSep-Va Ultra Plus (all commercially available from Millipore); Poros A and Mabcapture A (both commercially available from Poros); IPA-300, IPA-400 and IPA-500 (all commercially available from RepliGen Corp.); Affigel protein A and Affiprep protein A (both commercially available from Bio-Rad); Protein A Ceramic Hyper D F (commercially available from Pall Corporation); Ultralink Immobilized protein A and Agarose protein A (both commercially available from PIERCE); and Protein A Cellthru 300 and Protein A Ultraflow (both commercially available from Sterogen Bioseparations).

In another embodiment, the resin is CaptureSelect IgG-CH1 (suitable for purification of human IgG and all Fab fragments), CaptureSelect IgG-Fc (Hu) (specific for human IgG, recognizing all four subclasses), CaptureSelect LC-kappa (Hu) (suitable for purification of all human kappa Ig light chain containing products (previously known as CaptureSelect Fab kappa)), CaptureSelect LC-lambda (Hu) (suitable for purification of all human lambda Ig light chain containing products (previously known as CaptureSelect Fab lambda)), CaptureSelect IgG4 (Hu) (highly specific for human IgG4 without any crossbinding to other subclasses or species), CaptureSelect IgG1 (Hu) (highly specific for human IgG1 without any crossbinding to other subclasses or species), CaptureSelect IgG3 (Hu) (highly specific for human IgG3 without any crossbinding to other subclasses or species), CaptureSelect IgM (IgM resin suitable for human, mouse and rat IgM's), or CaptureSelect IgA (suitable for purification of human IgA, IgA-dimers and secretory IgA (sIgA)), all of which are commercially available from BAC. In another embodiment, the resin is IgSelect (an affinity medium for purification of human IgG), KappaSelect (an affinity medium for purification of Fab (kappa) fragments), LamdaFabSelect (an affinity medium for purification of lambda Fab fragments), or Capto L (a resin for capturing antibodies and antibody fragments), all of which are commercially available from GE Healthcare Life Sciences.

Further affinity chromatography systems which can be employed in the invention include, for example Protein G, Protein A/G and Protein L columns, each of which are also immunoglobulin-binding bacterial proteins with binding properties established in the art. Thus, an AC matrix that is a Protein G matrix, a Protein A/G matrix or a Protein L matrix can be used to purify antibodies, antibody fragments, or proteins comprising an Fc region (e.g., Fc fusion proteins).

Other non-limiting examples of AC matrices, and the types of proteins that they are effective in purifying include the following: an immobilized metal ion affinity chromatography (IMAC) column (for purification of proteins with an affinity for metal ions, such as histidine-tagged proteins), a calmodulin resin column (for purification of proteins tagged with calmodulin binding peptide (CBP)), a MEP HyperCel™ column (a cellulose matrix that selectively binds immunoglobulin), a column that binds maltose binding protein (MBP) (such as a Dextrin Sepharose™ resin that selectively binds proteins tagged with MBP), a column that binds glutathione-S-transferase (GST) (such as a Glutathione Sepharose™ resin that selectively binds proteins tagged with GST) and a column that binds Strep-Tag II (such as a Strep-Tactin™ Sepharose resin that selectively binds proteins tagged with Strep-Tag H). Furthermore, immunoaffinity matrices, which comprise an antibody as the target affixed to the solid phase, can be used to purify an antigen of interest that specifically binds to the antibody affixed to the solid phase.

While the invention of interest is described herein in particular with respect to purification of antibodies using Protein A chromatography, insofar as any protein (including fusion proteins) is known the art to selectively bind to a particular AC matrix, the protein is amenable to purification using the washing methods described herein.

As used herein, the term "antibody" includes whole antibodies and any antigen binding fragment (i.e., "antigen-binding fragments" (also known as "antigen-binding portions")) or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term "antibody" also encompasses multimeric forms of antibodies, such as minibodies, bis-scFv, diabodies, triabodies, tetrabodies and chemically conjugated Fab' multimers.

The term "antibody fragment" (also referred to as "antigen-binding fragment" or "antigen-binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) Nature 341:544-546), which consists, of a $V_H$ domain; (vii) an isolated complementarity determining region (CDR); and (viii) a nanobody (also known as a single-domain antibody (sdAb)), which is a heavy chain variable region containing a single variable domain and two constant domains. Single domain antibodies include $V_HH$ fragments (single-domain antibodies engineered from heavy-chain antibodies found in camelids, as well as $V_{NAR}$ fragments (single-domain antibodies obtained from heavy-chain antibodies (IgNAR, 'immunoglobulin new antigen receptor') of cartilaginous fishes).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Chimeric molecules (or fusion molecules) comprising an antigen binding domain, or equivalent, fused to another polypeptide or molecule are also encompassed by the present invention.

The wash solutions of the invention comprise arginine or an arginine derivative. The arginine which can be used in the present invention may be the natural amino acid arginine (e.g., L-arginine), D-arginine or an arginine derivative. As used herein, the term "arginine derivative" refers to molecules derived from the amino acid arginine, either the D or L-form, by chemical or physical processes that retain either zwitterionic, amphiprotic or dipolar properties of arginine (e.g., which may break non-specific interactions between impurities bound to the resin backbone, the protein A ligand or the bound target protein).

Non-limiting examples of arginine derivatives include acylated arginine, such as acetyl arginine and N-alpha-butyroyl-arginine, agmatine, arginic acid and N-alpha-pyvaloyl arginine. The arginine or arginine derivative can be used in the form of an acid addition salt. Examples of the acid which can form an acid addition salt include hydrochloric acid and the like. Other derivatives include, but are not limited to 3-Guanidinopropionic acid, 4-Guanidinobutyric acid, L-2-Amino-3-guanidinopropionic acid hydrochloride, L-2-Amino-3-guanidinopropionic acid hydrochloride, N$_\omega$Nitro-L-arginine benzyl ester p-toluenesulfonate salt and homoarginine.

The concentration of arginine or arginine derivative in the wash solution typically is between 0.05 and 0.85 M (which is the upper solubility of arginine in water at 20° C.) (e.g., 0.05 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M or 0.85 M), most preferably between 0.1 and 0.5 M (e.g., 0.1 M, 0.15 M, 0.2 M, 0.25 M, 0.3 M, 0.35 M, 0.4 M, 0.45 M or 0.5 M). In various embodiments, the concentration of arginine or arginine derivative can be, for example, 0.05 M, 0.1 M, 0.2M, 0.25M, 0.3M, 0.4 M, 0.5 M, 0.6 M, 0.7M or 0.8M, or between 0.1 M and 0.5 M. In certain embodiments, the concentration of arginine or arginine derivative in the wash solution is 0.25 M or greater. In particular embodiments, arginine is present at a concentration of 0.1 M or about 0.1 M, 0.25 M or about 0.25 M, or 0.5 M or about 0.5 M.

Although the invention is described herein with respect to a washing step during affinity chromatography, it will be readily apparent to the ordinarily skilled artisan that additional steps are carried out both before and after the washing step to achieve purification of the protein of interest from the affinity chromatography matrix. For example, prior to the washing and/or elution step, the methods of the invention can include an equilibration step, in which the affinity chromatography matrix is equilibrated, and/or a loading or capture step, in which a biochemical mixture (e.g., cellular harvest) containing the protein of interest is applied to the AC matrix.

Suitable equilibration buffers generally have approximately neutral pH to match the loading solution (~7.0+/−0.5) in order to prevent precipitation. It usually does not have to contain salt (NaCl), but just a buffer (phosphate for this pH range) at just high enough concentration to buffer (>about 20 mM). Suitable conditions for the equilibration buffer will vary depending upon the nature of the AC matrix and the protein of interest to be purified, and the ordinarily skilled artisan can readily determine such conditions using methods and information well established in the art. Non-limiting examples of the equilibration buffer for the purification of antibodies on Protein A columns are set forth in the Examples.

Additionally, after the washing step as mentioned above, the methods of the invention can include an elution step, in which an elution buffer is applied to the affinity chromatography matrix to elute the protein of interest from the matrix. Suitable conditions for the elution buffer will vary depending upon the nature of the AC matrix and the protein of interest to be purified, and the ordinarily skilled artisan can readily determine such conditions using methods and information well established in the art. Typically, elution of the protein of interest from the AC matrix is carried out at an acidic pH. Non-limiting examples of elution buffers for the purification of antibodies on Protein A columns are set forth in the Examples.

In another aspect, the invention provides methods for removing impurities from antibody-containing mixtures during Protein A purification of an antibody or other Fc containing protein. Accordingly, the invention provides a method of producing a purified antibody, antibody fragment, or protein comprising an Fc region using a Protein A column, the method comprising (a) loading a mixture comprising the antibody, antibody fragment, or protein, onto the Protein A column;

(b) washing the Protein A column with a wash solution comprising arginine, or an arginine derivative, at a pH of greater than 8.0 (e.g., a pH of greater than 8.1, preferably a pH of greater than 8.5, and more preferably between about 8.5-9.5 or about 8.9-9.0); and (c) eluting the antibody, antibody fragment, or protein from the Protein A column, wherein the wash is performed without the presence of a nonbuffering salt. Optionally, the method further comprises washing the Protein A column with an equilibration buffer prior to eluting the antibody, or antibody fragment, from the Protein A column. Optionally, the method can further comprise equilibrating the Protein A column prior to loading the protein of interest and/or prior to eluting the protein of interest.

Preferred concentrations and concentration ranges for the arginine (and arginine derivatives) are as described above. For example, in one embodiment, arginine is at a concentration of about 0.25 M or at a concentration of 0.25 M. In another embodiment, arginine is at a concentration in a range of 0.1-0.5 M. Preferred pHs and pH ranges also are as described above. For example, the pH is a pH of greater than 8.0 (e.g., preferably a pH of greater than 8.1, more preferably a pH of greater than 8.5, for example between about 8.5-9.5 or about 8.9-9.0).

The present invention is further illustrated by the following examples, which should not be construed as further limiting. In particular, the examples relate to preferred embodiments of the present invention. The contents of all references, patents and published patent applications cited throughout this application are expressly incorporated herein by reference in their entirety.

EXAMPLES

Example 1: High pH Alone Does Not Increase Product Purity

In this example, the effect of pH alone on the removal of impurities from an antibody-containing solution during affinity chromatography is assessed. Specifically, two wash solutions are compared: one containing 1 M NaCl at pH 7.0 and one containing 1 M NaCl at pH 9.0.

Clarified, mammalian cell culture supernatants containing between 0.2 and 3.0 g/L monoclonal antibody #1 are harvested by depth filtration and purified using an ALC column, in particular a Protein A column (GE Healthcare), according to the conditions described below in Table 1:

TABLE 1

Operating Conditions for Protein A Column for Example 1

| Step | Buffer | CV | RST * (min) | Comment |
|---|---|---|---|---|
| Equilibration | 20 mM $NaH_2PO_4$/$Na_2HPO_4$, pH 7.0 | 5 | 4 | |
| Load | Cell-free harvest ** | q.s. | 4 | |
| Wash 1 | Variable (See Table 2) | 6 | 4 | |
| Wash 2 | 20 mM $NaH_2PO_4$/$Na_2HPO_4$, pH 7.0 | 3 | 4 | |
| Elution | 20 mM Acetic acid | 5 | 4 | Peak collection (280 nm): 100-100 mAU |
| CIP | 0.1M NaOH | 4 | 4 | |
| Storage | 20 mM Acetic acid/Sodium acetate, 2% Benzylalkohol, pH 5.1 | 5 | 4 | |

* RST, residence time;
** Loading density: according to predetermined dynamic binding capacity: 36 g antibody per liter of resin The equilibrated column is loaded with clarified harvest and is first washed with either W1-N7 (1 M NaCl at pH 7.0) or W2-N9 (1 M NaCl at pH 9.0), as described in Table 2 below:

TABLE 2

List of Wash Solutions Tested

| Number | Buffer | Abbreviation of buffer |
|---|---|---|
| 1 | 20 mM $NaH_2PO_4$/$Na_2HPO_4$, 1M NaCl, pH 7.0 | W1-N7 |
| 2 | 20 mM $NaH_2$—/$Na_2H$—$PO4$/NaOH, 1M NaCl, pH 9.0 * | W2-N9 |

* pH adjusted with 1M Tris

The column is then washed with equilibration buffer as described in Table 1 (i.e., 20 mM $NaH_2PO_4$/$Na_2HPO_4$, pH 7.0), and then eluted at low pH. The eluate is analyzed for its antibody concentration by analytical ALC, for HMW/LMW by analytical size exclusion chromatography (SEC) and for HCP content by enzyme-linked immunosorbent assay, developed on the same cell line.

The percent yields for the Protein A purification of monoclonal antibody #1 using the two different wash solutions shown in Table 2, are shown below in Table 3.

TABLE 3

Comparison of Effect of Low and High pH on ALC Performance

| Run | Yield * (%) | Conc. (mg/ml) | HMW (%) | LMW (%) | HCP (ppm) |
|---|---|---|---|---|---|
| Load (clarified harvest) | | 2.32 | | | 370962 |
| W1-N7 | 100.8 | 20.00 | 1.3 | 0.4 | 9315 |
| W2-N9 | 101.9 | 20.28 | 1.2 | 0.5 | 8984 |

* Load in ml → Eluate in g

As shown in Table 3, varying the pH from neutral (pH 7.0) to basic (pH 9.0) has no effect on yield, eluate pool concentration, HMW or LMW species levels or HCP concentration. As such, these results demonstrate that high pH alone does not result in increased product purity. However, as demonstrated in the following examples, high pH in combination with arginine has a significant effect on product purity.

Example 2: Arginine (in Combination with High pH) is a Crucial Excipient

In this example, the ability of various washes is compared to determine which wash and pH is the most effective in removing impurities from an antibody-containing solution during affinity chromatography. Specifically, four wash solutions are compared: one containing 1 M NaCl at pH 7.0, one containing 250 mM arginine at pH 7.0, one containing 250 mM arginine at pH 8.9, and one containing 500 mM Tris at pH 8.9. Tris is included to determine whether Tris alone has an effect on removing impurities.

Clarified, mammalian cell culture supernatants containing between 0.2 and 2.5 g/L monoclonal antibody #3 are harvested by depth filtration and purified using an ALC column, in particular a Protein A column (GE Healthcare), according to the conditions described below in Table 4:

TABLE 4

Operating Conditions for Protein A Column for Example 2

| Step | Buffer | CV | RST * (min) | Comment |
|---|---|---|---|---|
| Equilibration 1 | 20 mM $NaH_2PO_4$/ $Na_2HPO_4$, pH 7.0 | 3 | 4 | |
| Equilibration 2 | Buffer of Wash 1 | 3 | 4 | |
| Load | Cell-free harvest | q.s. | 4 | |
| Wash 1 | Variable (See Table 5) | 6 or 12 | 4 | |
| Wash 2 | 20 mM $NaH_2PO_4$/ $Na_2HPO_4$, pH 7.0 | 3 | 4 | |
| Elution | 50 mM Acetic acid | 5 | 4 | Peak collection (280 nm): 100-100 mAU |
| CIP | 0.1M NaOH | 3 | 4 | |
| Storage | 20 mM Na-acetate, 2% Benzylalkohol, pH 5.1 | 5 | 4 | |

* RST, residence time;
** Loading density: 30 g antibody per liter of resin

The equilibrated column is loaded with clarified harvest and is first washed with either W1-N7, W3-Arg7, W4-Arg9 or W5-T9, as described in Table 5 below:

TABLE 5

List of Wash Solutions Tested

| Number | Buffer | Abbreviation of buffer |
|---|---|---|
| 3 | 20 mM $NaH_2PO_4$/$Na_2HPO_4$, 1M NaCl, pH 7.0 | W1-N7 |
| 4 | 250 mM L-arginine, pH 7.0 ** | W3-Arg7 |
| 5 | 250 mM L-arginine, pH 8.9 ** | W4-Arg9 |
| 6 | 500 mM Tris, pH 8.9 | W5-T9 |

** pH adjusted with 1M Tris

The column is then washed with equilibration buffer as described in Table 4 (i.e., 20 mM $NaH_2PO_4$/$Na_2HPO_4$, pH 7.0), and then eluted at low pH. The eluate is analyzed for its antibody concentration by analytical ALC, for HMW/LMW by analytical size exclusion chromatography (SEC) and for HCP content by enzyme-linked immunosorbent assay, developed on the same cell line.

The percent yields for the Protein A purification of monoclonal antibody #3 using the four different wash solutions shown in Table 5, are shown below in Table 6.

TABLE 6

Comparison of NaCl-Containing ALC Wash Buffer to Arginine-Based Buffer at Different pH Values and Tris-Based Buffer

| Name | Yield (%) * | Conc (g/L) | HMW (%) | LMW (%) | HCP (ppm) |
|---|---|---|---|---|---|
| Harvest | — | 1.53 | | | >600000** |
| W1-N7 | 100.1 | 17.13 | 3.1 | 0.6 | 32000 |
| W3-Arg7 | 99.1 | 18.94 | 2.3 | 0.4 | 28273 |
| W4-Arg9 | 99.3 | 19.72 | 1.5 | 0.1 | 9210 |
| W5-T9 *** | 98.1 | 16.44 | 3 | 0.6 | 54876 |

* Load in ml → Eluate in g;
**HCP value not determined exactly;
*** wash was performed for 12 CVs instead of 6

As shown in Table 6, it is evident that the arginine-based buffers are more efficient in removing HMWs, LMWs and HCPs than a high salt-based wash. Moreover, this effect is amplified at high pH conditions. Specifically, using an arginine-containing wash buffer at high pH of 8.9 (W4-Arg9), without the presence of a nonbuffering salt, results in a 3-fold reduction of HCPs, a 4-fold reduction of LMW levels, and a reduction of the aggregate level from 2.3 to 1.5%, as compared to an arginine-containing wash buffer at pH of 7.0 (W3-Arg7). Despite comparable yields, the higher pH also increases the pool concentration.

Since Tris is used to adjust the pH in the arginine-containing buffers and close to 300 mM Tris is required to achieve a pH of 8.9, a wash containing 500 mM Tris at high pH (i.e., W5-T9) is included. However, as shown in Table 6, W5-T9 has no effect on the removal of HMWs or LMWs. In fact, the HCP level is even higher for W5-T9 than for the NaCl-containing wash. Given that this wash is performed at best-case conditions for Tris (e.g., meaning almost double Tris concentration as compared to the highest concentration used in the other buffers and doubling of the washing time), the results suggest that Tris alone has no wash effect. Furthermore, it is clear that high pH alone does not result in the desired impurity removal.

Example 3: Arginine Wash in Combination with High pH Significantly Reduces Impurities In this example, the effect of three different wash buffer conditions on the purity of three monoclonal antibodies is assessed. Specifically, three wash solutions are compared: (1) low pH (W6-Ace5), (2) high salt (W1-N7), (3) and arginine at high pH (W7-Arg9).

Three monoclonal antibodies (#1, #2, and #4) were harvested by depth filtration and purified using an ALC column, in particular a Protein A column (GE Healthcare), according to the conditions described below in Table 7:

TABLE 7

Operating Conditions for Protein A Column for Example 4

| Step | Buffer | CV | RST * (min) |
|---|---|---|---|
| Equilibration | 20 mM $NaH_2PO_4$/$Na_2HPO_4$, pH 7.0 (LOESL0073) | 6 | 4 |
| Load | Cell-free harvest ** | q.s. | 4 |
| Wash 1 | Variable (See Table 11) | 3 | 4 |
| Wash 2 | 20 mM $NaH_2PO_4$/$Na_2HPO_4$, pH 7.0 *** | 3 | 4 |
| Elution | 20 mM Acetic acid | 4 | 4 |

TABLE 7-continued

Operating Conditions for Protein A Column for Example 4

| Step | Buffer | CV | RST* (min) |
|---|---|---|---|
| CIP | 0.1M NaOH | 3 | 4 |
| Storage | 20 mM Acetic acid/Sodium acetate, 2% Benzylalkohol, pH 5.1 | 4 | 4 |

* RST, residence time;
** Loading density: according to predetermined dynamic binding capacity: 36/42/36 g antibody By/Qg/Bp, respectively per liter of resin;
*** Step omitted if wash 1 was 20 mM sodium acetate, pH 5.0.

The equilibrated column is loaded with clarified harvest and is first washed as described in Table 8 below:

TABLE 8

List of wash solutions tested

| Number | Buffer | Abbreviation of buffer |
|---|---|---|
| 1 | 20 mM Na-acetate, pH 5.0 | W6-Ace5 |
| 2 | 20 mM NaH$_2$—/Na$_2$H—PO4, 1M NaCl, pH 7.0 | W1-N7 |
| 3 | 250 mM L-arginine/L-arginine-HCl, pH 9.0 * | W7-Arg9 |

* similar to W4-Arg9, but pH adjustment with L-arginine, not with Tris

The column is then washed with equilibration buffer as described in Table 7 (i.e., 20 mM NaH$_2$PO$_4$/Na$_2$HPO$_4$, pH 7.0), and then eluted at low pH. The eluate is analyzed for its antibody concentration by analytical ALC, for HMW/LMW by analytical size exclusion chromatography (SEC) and for HCP content by enzyme-linked immunosorbent assay, developed on the same cell line.

Table 9 summarizes the effects of different ALC wash buffer conditions on the purity of three monoclonal antibodies in the eluate, as assessed by antibody yield, eluate pool concentrations, levels of HCP and levels of HMW.

TABLE 9

Summary of Comparison of the ALC performance After Washing with Low pH (W6-Ace5), High Salt (W1-N7) or Arginine at High pH (W7-Arg9) for Three Monoclonal Antibodies (#1, #2, and #4)

| mAb | Wash buffer | Yield [%] | Conc. (g/L) | HCP [ppm] | HMW [%] |
|---|---|---|---|---|---|
| #1 | Harvest | NA | 2.29 | 381238 | NA |
| #1 | W6-Ace5 | 84.5 | 16.2 | 35287 | 3.9 |
| #1 | W1-N7 | 100 | 20.0 | 9315 | 1.3 |
| #1 | W7-Arg9 | 98.6 | 19.9 | 10755 | 1.0 |
| #4 | Harvest | NA | 1.91 | 253087 | NA |
| #4 | W6-Ace5 | 92.7 | 19.5 | 17981 | 2.8 |
| #4 | W1-N7 | 97.6 | 19.0 | 14894 | 1.3 |
| #4 | W7-Arg9 | 94.1 | 20.7 | 6679 | 0.9 |
| #2 | Harvest | NA | 1.72 | 603649 | NA |
| #2 | W6-Ace5 | 94.8 | 16.1 | 11001 | 8.8 |
| #2 | W1-N7 | 98.5 | 16.4 | 6607 | 8.4 |
| #2 | W7-Arg9 | 98.8 | 13.7 | 1759 | 8.3 |

The bolded rows represent the composition of the harvest; Conc, eluate concentration; HCP, host cell protein; HMW, high molecular weight species; LRV, log reduction value; NA, not applicable.

As shown above in Table 9, washing with low pH (W6-Ace5) results in yields between 84.5 and 94.8% (average: 90.7%) and washing with high salt (W1-N7) results in an average yield of 98.7% (between 97.6 and 100%). Washing with arginine at high pH (W7-Arg9) results in the highest yield of all three washes, with an average of 97.2% yield (between 94.1 and 98.8%).

The eluate concentrations do not show a clear trend when comparing the different wash buffer applied during ALC with the different antibodies. Overall, comparable ranges are found and neither wash consistently results in the lowest or highest concentration.

With respect to impurity removal, a general order can be established between the three wash buffers. The lowest HCP reduction is consistently obtained with the low pH wash (W6-Ace5), followed by the high salt wash (W1-N7). The highest impurity removal is obtained with the arginine, high pH 9.0 wash (W7-Arg9). Specifically, in terms of logarithmic order of removal, an average of 1.3 logs is obtained after washing with the low pH wash (W6-Ace5), 1.6 logs is obtained after washing with the high salt wash (W1-N7) and the highest removal of 1.9 logs is achieved after washing with the arginine, high pH 9.0 wash (W7-Arg9).

With respect to HMW levels, these levels are heterogeneous for the three different monoclonal antibodies and the removal of HMWs is monoclonal antibody-dependent. Overall, the low pH wash (W6-Ace5) is the least effective washing solution at reducing HMW levels. Better results are obtained with the high salt wash (W1-N7). However, the lowest HMW values in the ALC eluate are consistently found with the arginine, high pH 9.0 wash (W7-Arg9). Two monoclonal antibodies respond with a 3.1 or 3.9-fold reduction in HMWs, respectively from the low pH wash (W6-Ace5) as compared to the high pH 9.0 wash (W7-Arg9), whereas monoclonal antibody #2 only shows a marginal reduction.

In sum, this example demonstrates that the novel combination of an arginine and high pH significantly improves antibody purity and concentration as compared to standard wash buffers, as measured by yield, pool concentration, HCP pool content and HMW pool level. Washing with the specific combination of arginine and high pH results in higher product purity and higher eluate concentration, while simultaneously minimizing product loss. Further, the decrease in HCP and HMW levels reduces the burden on subsequent downstream processing steps and increases the overall process performance in terms of quality and profitability. Additionally, as any contaminant such as HCPs or HMW species may serve as nuclei for further product aggregation, their reduction during the capture step will slow down impurity-related aggregation processes.

What is claimed is:

1. A method of producing a purified protein of interest using an affinity chromatography (AC) matrix to which the protein of interest is bound, the method comprising washing the AC matrix with a wash solution comprising arginine, or an arginine derivative, at a pH of at least 8.5, and thereafter eluting the protein of interest from the AC matrix, wherein the wash is performed without the presence of a nonbuffering salt.

2. The method of claim 1, wherein the method comprises:
    a) loading a mixture comprising the protein of interest onto the AC matrix;
    b) washing the AC matrix with a wash solution comprising arginine, or an arginine derivative, at a pH at least 8.5; and
    c) eluting the protein of interest from the AC matrix, wherein the wash is performed without the presence of a nonbuffering salt.

3. The method of claim 1, wherein the protein of interest is an antibody, antibody fragment, or Fc fusion protein.

4. The method of claim 3, wherein the AC matrix is a Protein A column.

5. The method of claim 1, wherein the pH is 8.5-9.5.

6. The method of claim 1, wherein the pH is about 8.9-9.0.

7. The method of claim 1, wherein the pH is 9.0 or about 9.0.

8. The method of claim 1, wherein the arginine derivative is selected from the group consisting of acetyl arginine, agmatine, arginic acid, N-alpha-butyroyl-L-argimine and N-alpha-pyvaloyl argimine.

9. The method of claim 1, wherein arginine is at a concentration in a range of 0.1-0.5 M.

10. The method of claim 9, wherein arginine is at a concentration of or about 0.25 M.

11. The method of claim 1, wherein the wash solution comprises arginine-HCl.

12. A method of producing a purified antibody, antibody fragment, or Fc fusion protein using a Protein A column, the method comprising
   a. loading a mixture comprising the antibody, antibody fragment, or Fc fusion protein onto the Protein A column;
   b. washing the Protein A column with a wash solution comprising arginine, or an arginine derivative, at a pH at least 8.5; and
   c. eluting the antibody, antibody fragment, or Fc fusion protein from the Protein A column,
wherein the wash is performed without the presence of a nonbuffering salt.

13. The method of claim 12, further comprising equilibrating the Protein A column with an equilibration buffer prior to loading and/or eluting the antibody, antibody fragment, or Fc fusion protein from the Protein A column.

\* \* \* \* \*